(12) United States Patent
Yuyama

(10) Patent No.: US 7,988,400 B2
(45) Date of Patent: Aug. 2, 2011

(54) VIAL CONVEYANCE DEVICE AND ARM FOR THE SAME

(75) Inventor: Shoji Yuyama, Osaka (JP)

(73) Assignee: Yuyama Mfg. Co., Ltd., Toyonaka-shi (JP)

( * ) Notice: Subject to any disclaimer, the term of this patent is extended or adjusted under 35 U.S.C. 154(b) by 971 days.

(21) Appl. No.: 11/816,671

(22) PCT Filed: Feb. 21, 2006

(86) PCT No.: PCT/JP2006/303017
§ 371 (c)(1),
(2), (4) Date: Aug. 20, 2007

(87) PCT Pub. No.: WO2006/090683
PCT Pub. Date: Aug. 31, 2006

(65) Prior Publication Data
US 2009/0016852 A1    Jan. 15, 2009

(30) Foreign Application Priority Data

Feb. 24, 2005  (JP) ................................. 2005-049314

(51) Int. Cl.
*B65H 1/00* (2006.01)
(52) U.S. Cl. ...................... 414/222.01; 294/94; 221/265

(58) Field of Classification Search ................... 294/94, 294/95; 414/222.01, 222.12; 221/265
See application file for complete search history.

(56) References Cited

U.S. PATENT DOCUMENTS

| | | | |
|---|---|---|---|
| 4,340,249 A * | 7/1982 | Bucklew | 294/95 |
| 4,673,545 A * | 6/1987 | Cooke et al. | 376/261 |
| 5,208,762 A | 5/1993 | Charhut et al. | |
| 5,337,919 A | 8/1994 | Spaulding et al. | |
| 5,527,078 A * | 6/1996 | Messick | 294/95 |
| 5,798,020 A | 8/1998 | Coughlin et al. | |
| 5,946,883 A * | 9/1999 | Yuyama et al. | 53/154 |
| 7,384,085 B2 * | 6/2008 | Steinhovden | 294/95 |
| 2005/0046213 A1 * | 3/2005 | Geddo | 294/95 |

FOREIGN PATENT DOCUMENTS

| | | |
|---|---|---|
| JP | 58 117337 | 8/1983 |
| JP | 58-117337 | 8/1983 |
| JP | 2 117888 | 9/1990 |
| JP | 2 48399 | 10/1990 |
| JP | 2-48399 | 10/1990 |
| JP | 11 70901 | 3/1999 |

* cited by examiner

*Primary Examiner* — Charles A Fox
(74) *Attorney, Agent, or Firm* — Oblon, Spivak, McClelland, Maier & Neustadt, L.L.P.

(57) ABSTRACT

A vial conveyance device which includes, in order to hold and release a vial, at least two arms that can be opened and closed, an urging member that urges the arms in an opening direction, a frame body for opening and closing the arms, and a frame body stopper that stops the frame body in a state in which the arms are closed.

9 Claims, 8 Drawing Sheets

VIAL CONVEYANCE DEVICE AND ARM FOR THE SAME

BACKGROUND OF THE INVENTION

1. Technical Field

The present invention relates to a vial conveyance device for conveying a vial filled with tablets in a tablet filling device and to an arm for the same.

2. Background Art

In many cases, a tablet filling device or the like for filling a vial with tablets includes, as a component thereof, a vial conveyance device for conveying a vial from a predetermined position to another position. When, in particular, a high-speed and accurate positioning is required, the vial conveyance device uses, apart from a conveyor and an ascent/descent table, a robot arm in which there are provided on a movable base a pair of grasping members that can be opened and closed by a motor or the like as described in Patent Document 1.

Patent Document 1: JP 11-70901 A
Patent Document 2: U.S. Pat. No. 5,798,020
Patent Document 3: U.S. Pat. No. 5,337,919
Patent Document 4: U.S. Pat. No. 5,208,762

However, such a robot arm is composed of a plurality of drive mechanisms, so it has a problem in that it involves a complicated and heavy structure, consumes a lot of energy, and requires a complicated control, resulting in high cost.

BRIEF SUMMARY OF THE INVENTION

In view of the above problem with the prior art, it is an object of the present invention to provide a vial conveyance device that is capable of conveying a vial with a simple construction and an arm for the same.

In order to solve the above-mentioned problem, a vial conveyance device according to the present invention for conveying a vial from a receiving position to a delivery position includes: at least two arms that can be opened and closed so as to hold and release the vial; an urging member that urges the arms so as to hold the vial; a frame body that reciprocates parallel to a conveying direction of the vial to open and close the arms; a frame body stopper that stops the frame body in a state in which the arms release the vial; an arm moving device that moves the arm to a receiving position and a delivery position for the vial; a first abutment member that abuts against the frame body when the arm moves to the receiving position to release the frame body from the frame body stopper and to hold the vial with the arms; and a second abutment member that abuts against the frame body when the arm moves to the delivery position to engage the frame body with the frame body stopper and to release the arms from the vial.

The receiving position is a position where a vial from another device is received by the vial conveyance device of the present invention, and the delivery position is a position where the vial conveyed by the vial conveyance device of the present invention is delivered to another device. Those positions may be arranged either vertically or horizontally. While it is desirable, for simplification in structure, to provide two (a pair of) arms, it is also possible to provide three or four (two pairs of) arms taking safety into consideration. In the case of two arms, they may be supported by a single rotation shaft so as to cross each other or they may be separately supported by two rotation shafts. The urging member may exert an urging force so as to hold the inner surface of a vial, that is, so as to open the forward ends of the arms. Conversely, the urging member may exert an urging force so as to hold the outer surface of the vial, that is, so as to close the forward ends of the arms. While it is possible to use various spring means, such as a coil spring and a plate spring, as the urging member, an arm having resiliency can be used. While the frame body may be of a rectangular configuration surrounding the arms, this should not be construed restrictively; it is possible to adopt an arbitrary configuration such as a U-shaped one formed of a square with one side removed therefrom or a circular one.

In the vial conveyance constructed as described above, when the arms are moved to the receiving position by an arm moving device, with the frame body engaged with the frame body stopper, the first abutment member abuts against the frame body to release the frame body from the frame body stopper, so the arms can hold and receive a vial. When the arms are moved to the receiving position by the arm moving device, the second abutment member abuts against the frame body to engage the frame body with the frame body stopper, so the arms can release and deliver the vial.

It is preferable that a guide groove be provided in the arms to extend in a moving direction of the frame body, and the frame body be equipped with a roller rolling in the guide groove. In this case, the frame body stopper is preferably formed in the guide groove and is a recess to be engaged with the roller.

The arm moving device preferably conveys the arm with a forward end thereof directed downwardly.

The first abutment member is preferably an opening edge portion of the vial prepared at the receiving position.

According to an aspect of an arm for a vial conveyance device according to the present invention, there is provided an arm for a vial conveyance device for conveying a vial from a receiving position to a delivery position including: at least two arms that can be opened and closed so as to hold and release the vial; an urging member that urges the arms so as to hold the vial; a frame body that reciprocates parallel to a conveying direction of the vial to open and close the arms; a frame body stopper that stops the frame body in a state in which the arms release the vial, in which the frame body is caused to abut against an abutment member and to be reciprocated for opening and closing the arms.

Further, according to another aspect of an arm for a vial conveyance device according to the present invention, there is provided an arm for a vial conveyance device for conveying a vial from a receiving position to a delivery position including: at least two arms that can be opened and closed so as to hold and release the vial; an urging member that urges the arms so as to hold the vial; a frame body that reciprocates parallel to a conveying direction of the vial to open and close the arms; a frame body stopper that stops the frame body in a state in which the arms release the vial, in which the frame body is caused to abut against an abutment member and to be reciprocated, when the arm moves to the receiving position and the delivery position, for opening and closing the arms.

It is preferable that a guide groove be provided in the arms to extend in a moving direction of the frame body, and the frame body be equipped with a roller rolling in the guide groove. In this case, the frame body stopper is preferably formed in the guide groove and is a recess to be engaged with the roller.

According to the vial conveyance device of the present invention, the arms are moved by the arm moving device, and the frame body is engaged with or disengaged from the frame body stopper by the first abutment member and the second abutment member, whereby it is possible to convey the vial from the receiving position to the delivery position. In this way, there is no need to provide a drive source for opening and closing the arms, so the construction and control of the device are simplified. Further, the weight of the moving portions is reduced, so the capacitance of the drive source may also be smaller.

Further, according to the arm for the vial conveyance device of the present invention, the arms can be opened and closed solely by abutting the frame body against the abutment member, and there is no need to provide a drive source for opening and closing the arms, so the construction and control of the device are simplified. Further, the weight of the moving portions is reduced, so the capacitance of the drive source may also be smaller.

Figure 1:
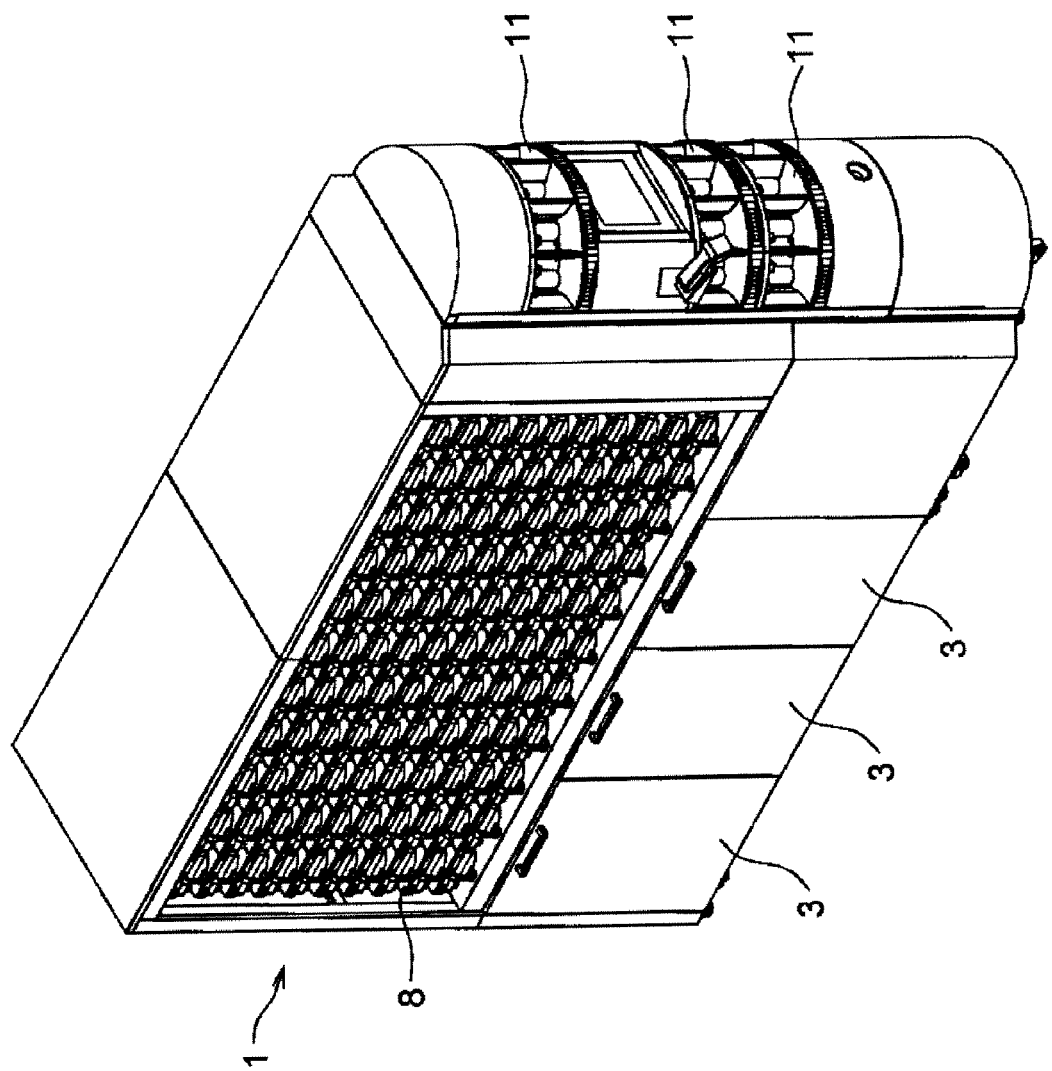
FIG. 1 is a perspective view of a tablet filling device equipped with a vial conveyance device according to the present invention.

DESCRIPTION OF REFERENCE SYMBOLS 2 vial
2a opening edge portion (first abutment member)
3 vial supply device
4 first conveyance device
5 fork support device
6 fourth conveyance device (vial conveyance device)
7 third conveyance device
8 tablet cassette
10 capping device
12 frame
13 first rail
14 second rail
15 first slider
16 second slider
17 ascent/descent arm
18 motor (arm moving device)
19 feed screw (arm moving device)
20 nut
21 mounting plate
22 mounting member
23 box body
24 base plate
25 rotation shaft
26 arm
26a stopper portion
26b guide groove
27 frame body
28 suspension member
29 abutment member (second abutment member)
30 buffer spring
31 opening spring (urging member)
32 roller
33 pin
P1 vial receiving position
P2 vial delivery position

DETAILED DESCRIPTION OF THE INVENTION

An embodiment of the present invention will be described with reference to the drawings.

FIG. 1 shows a tablet filling device 1 equipped with a vial supply device according to the present invention. The tablet filling device 1 fills vials 2 with tablets based on prescription data, and is equipped with three vial supply devices 3, a first conveyance device 4, a fork support device 5, a labeling device 5A, a second conveyance device 6, a third conveyance device 7, a large number of tablet cassettes 8 arranged in a regular fashion, a fourth conveyance device 9, a capping device 10, and extraction ports 11 arranged in three stages.

In the tablet filling device 1, the vial supply devices 3 can accommodate a large number of vials 2, and supply a vial 2 as needed to the first conveyance device 4 by a lifter (not shown). The first conveyance device 4 is composed of small belt conveyors 4a which receive vials 2 supplied from each of the vial supply devices 3 and convey the vials 2, and a large belt conveyor 4b which receives the vials 2 conveyed from each of the small belt conveyors 4a and convey the vials 2. The first conveyance device 4 supplies the vials 2 discharged from each of the vial supply devices 3 to the fork support device 5. As shown in FIG. 3(B), the fork support device 5 is formed of a fork-like movable frame 5a supporting the neck portions of the vials 2 of different sizes. The fork support device 5 is capable of horizontally moving between a receiving position where the vials 2 supplied from the first conveyance device 4 are received, a labeling position where the received vials 2 are opposed to the labeling device 5A, and a delivery position where the vials 2 that have undergone labeling are delivered to the second conveyance device 6. Under the movable frame 5a, there is provided a guide plate 5b for moving the vials 2 to the forward end of the fork when the movable frame 5a moves from the receiving position to the labeling position. The labeling device 5A rotates the vials 2 supported by the fork support device 5 and, while doing so, affixes labels to the peripheral surfaces thereof.

The second conveyance device 6 is a vial conveyance device according to the present invention; as described in detail below, it receives a labeled vial 2 from the fork support device 5 prepared at the delivery position, and raises it vertically to deliver it to the third conveyance device 7. The third conveyance device 7 moves the vial 2 to a designated tablet cassette 8, and receives in the vial 2 a designated amount of tablets discharged from the tablet cassette 8. The fourth conveyance device 9 receives the vial 2 containing tablets from the third conveyance device 7, and moves it to the capping device 10. The capping device 10 threadedly engages a cap with the vial 2 to seal it. Further, the fourth conveyance device places the vial 2 with the cap fastened thereto at any one of the extraction ports 11, enabling a patient or an operator to extract the vial 2 filled with tablets.

Subsequently, the fourth conveyance device 6 of this embodiment of the present invention will be described in detail.

Figure 4:
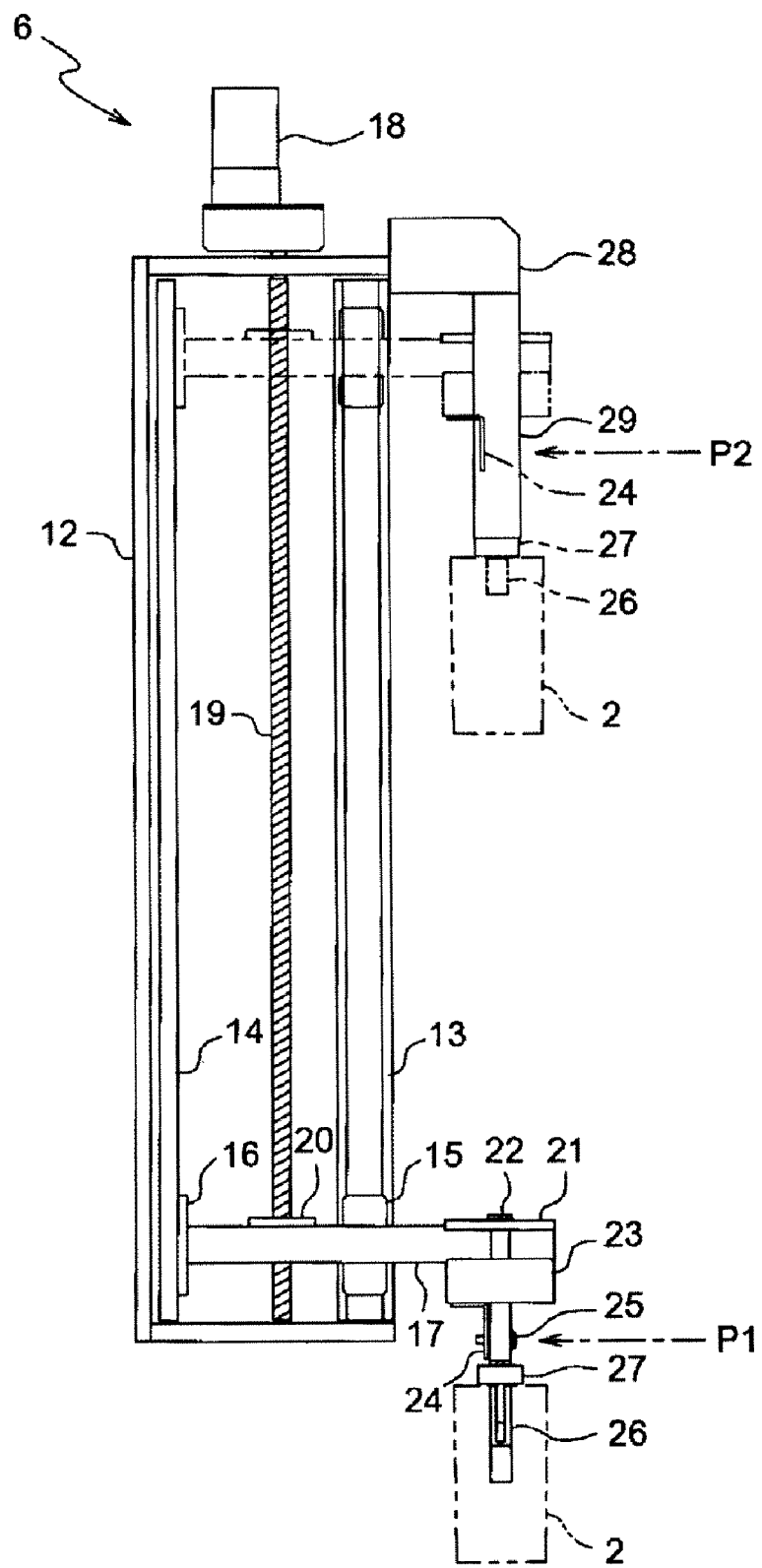
FIG. 4 is a front view of a vial conveyance device according to a first embodiment of the present invention.
Figure 5:
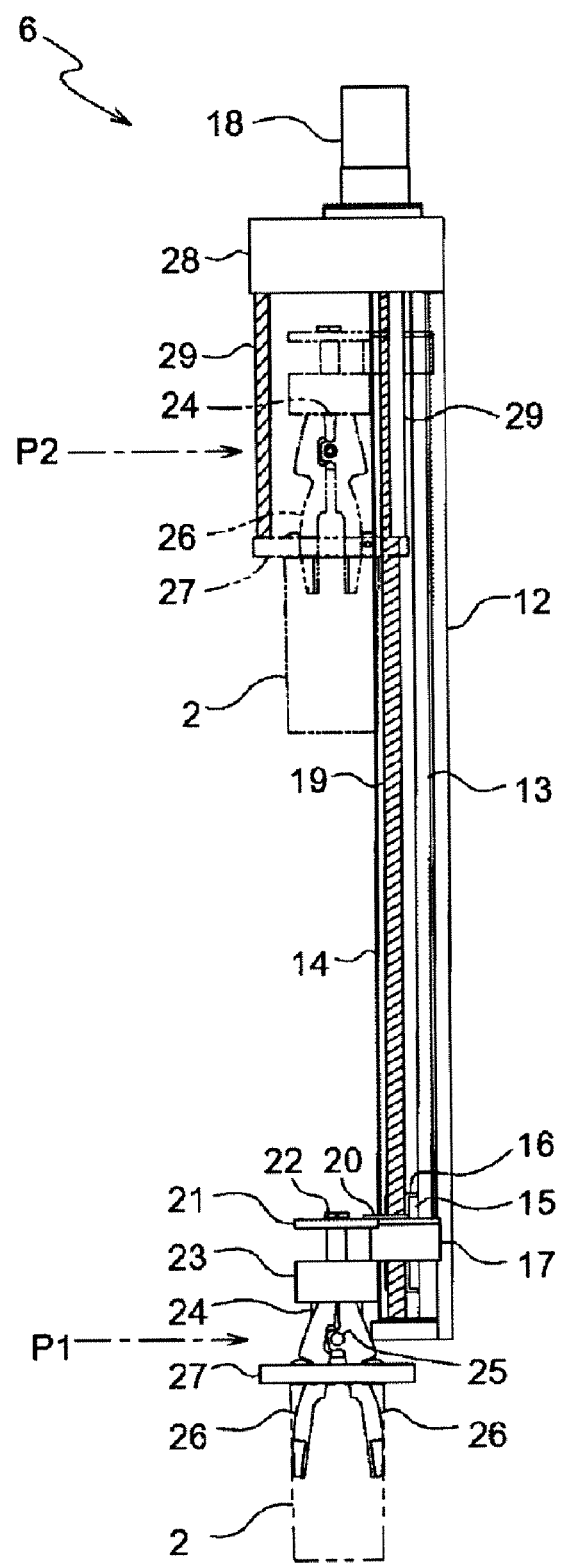
FIG. 5 is a side view of the vial conveyance device of FIG. 4.

FIGS. 4 and 5 are a front view and a side view of the fourth vial conveyance device 6, respectively. The conveyance device of this embodiment is formed by a frame 12 composed of two upright plates parallel to each other and horizontal plates connected to the upper and lower ends of the upright plates; a first rail 13 and a second rail 14 that are vertically provided to the respective upright plates of the frame 12, and a horizontal ascent/descent arm 17 is mounted to a first slider 15 and a second slider 16 mounted so as to be movable along the first rail 13 and the second rail 14, respectively. A nut 20, which is moved vertically by an upright feed screw 19 rotated by a motor 18 provided on the top portion of the frame 12, is mounted onto the ascent/descent arm 17, with the ascent/descent arm 17 being moved vertically up and down. A mounting plate 21 is fixed to the forward end of the ascent/descent arm 17 so as to protrude horizontally, and a box body 23 is vertically suspended by a mounting member 22 extending through the mounting plate 21. A base plate 24 serving as a base is fixed to the box body 23, and a pair of arms 26 are pivoted to a horizontal rotation shaft 25 provided to the base plate 24 so as to be capable of being opened and closed, with their lower ends moving toward and away from each other. A frame body 27 is provided so as to surround the arms 26; the lower ends of the arms 26 are opened by being moved away from each other within the vial 2, thereby making it possible to hold the vial 2 by the arms 26 as indicated by a chain double-dashed line. Further, two abutment members 29 are suspended from a suspension member 28 provided on the top portion of the frame 12. Through vertical movement of the ascent/descent arm 17, the base plate 24 is caused to ascend and descend between a vial receiving position P1 and a vial delivery position P2.

Figure 6:
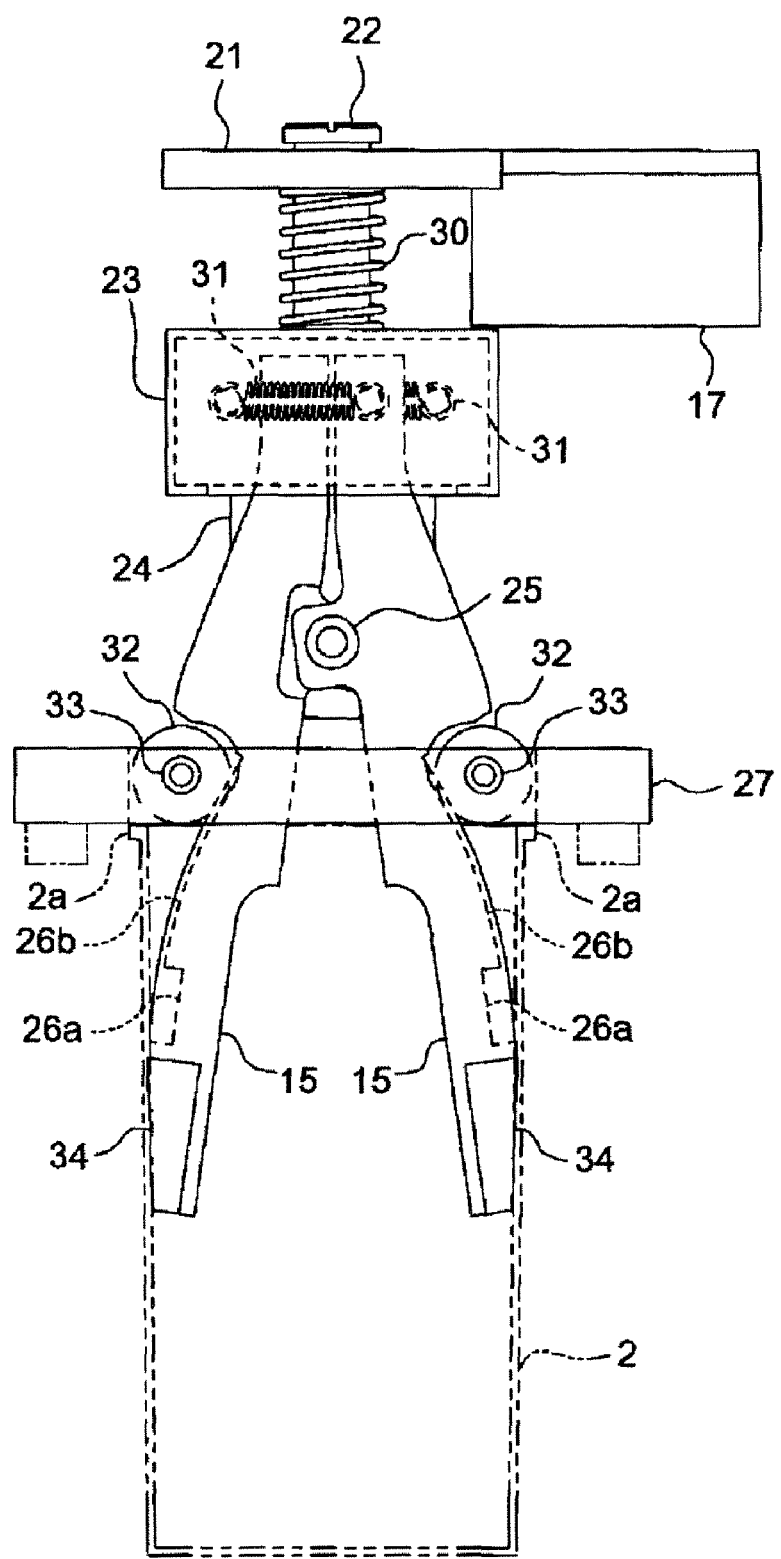
FIG. 6 is an enlarged partial view of the vial conveyance device of FIG. 4.

Next, FIG. 6 is an enlarged view of the forward end portion of the ascent/descent arm 17. The mounting member 22 extends through the mounting plate 21, and is vertically movable; a buffer spring 30 is mounted to the periphery of the mounting member 22, urging the mounting plate 21 and the box body 23 away from each other. The box body 23 can be brought close to the mounting plate 21 by compressing the buffer spring 30. With this construction, an external force applied through the arms 26 is absorbed, and no large shock is applied to the ascent/descent arm 17. The upper end portions of the two arms 26, which are pivoted to the base plate 24 by the rotation shaft 25, extend within the box body 23, and are urged by an opening spring 31 serving as an urging member mounted onto the upper end portions such that the respective lower ends move away from each other for opening. Two rollers 32 are rotatably mounted to the frame body 27 by pins 33, holding the arms 26 therebetween. Each arm 26 has in the side surface thereof a stopper portion 26a provided as a somewhat deep recess and a guide groove 26b of a shallow groove extending upwardly from the stopper portion 26a along the arm 26, and the roller 32 can move to the stopper portion 26a along the guide groove 26b. Friction members 34 made of rubber are mounted to the forward end portions of the arms 26. When the arms 26 are opened by the urging force of the opening spring 31, and the forward ends of the arms 26 are brought into contact with the inner wall of the vial 2, the friction members 34 increase the friction between the arms 26 and the vial 2, enabling the arms 26 to reliably hold the vial 2. In FIG. 6, the frame body 27 abuts against the opening edge portion 2a of the vial 2, and is at a release position where the rollers 32 abuts against the guide grooves 26b near the upper ends thereof, with the vial 2 being held by opening the arms 26 by the urging force of the opening spring 31. Meanwhile, in FIG. 7, the frame body 27 is at an engagement position where the rollers 32 are engaged with the stopper portions 26a, with the arms 26 being closed against the urging force of the opening spring 31. Here, the guide grooves 26b, which are opposed to each other, are formed such that the distance therebetween decreases as getting away from the stopper portions 26a and getting closer to the rotation shaft 25. FIG. 8 is a sectional view taken along the line VIII-VIII of FIG. 7. The frame body 27 surrounds the paired arms 26. The thickness of the rollers 32, rotatably supported by the pins 33, is approximately one third of the thickness of the arms 26, with the rollers being fitted into the stopper portions 26a provided to the side surfaces of the arms 26 to be engaged therewith. As a result, the arms 26 and the frame body 27 are not brought into direct contact with each other.

Subsequently, the operation of the vial conveyance device 6, constructed as described above, will be described.

Figure 2:
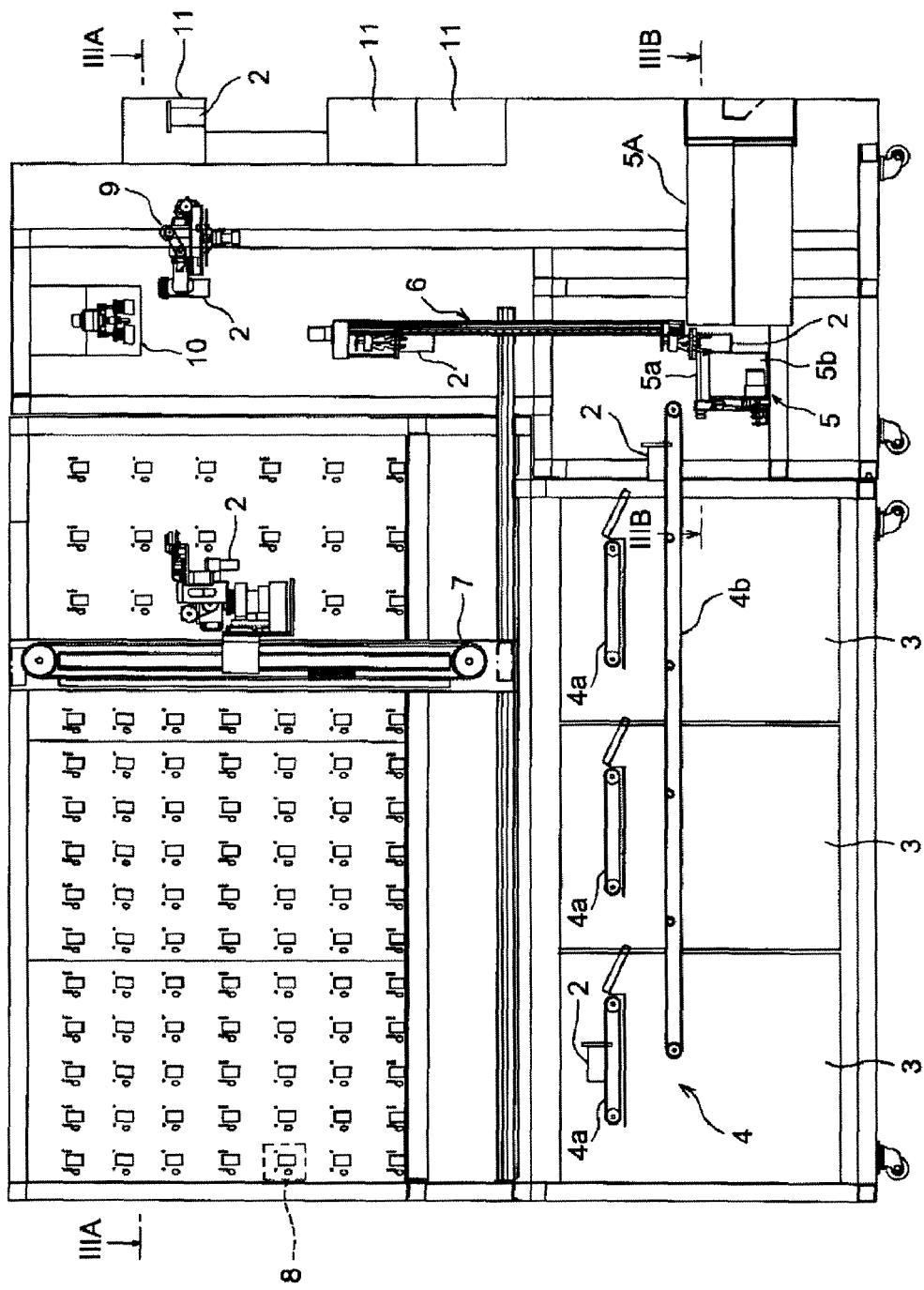
FIG. 2 is an elevation sectional view of the tablet filling device of FIG. 1.
Figure 3:
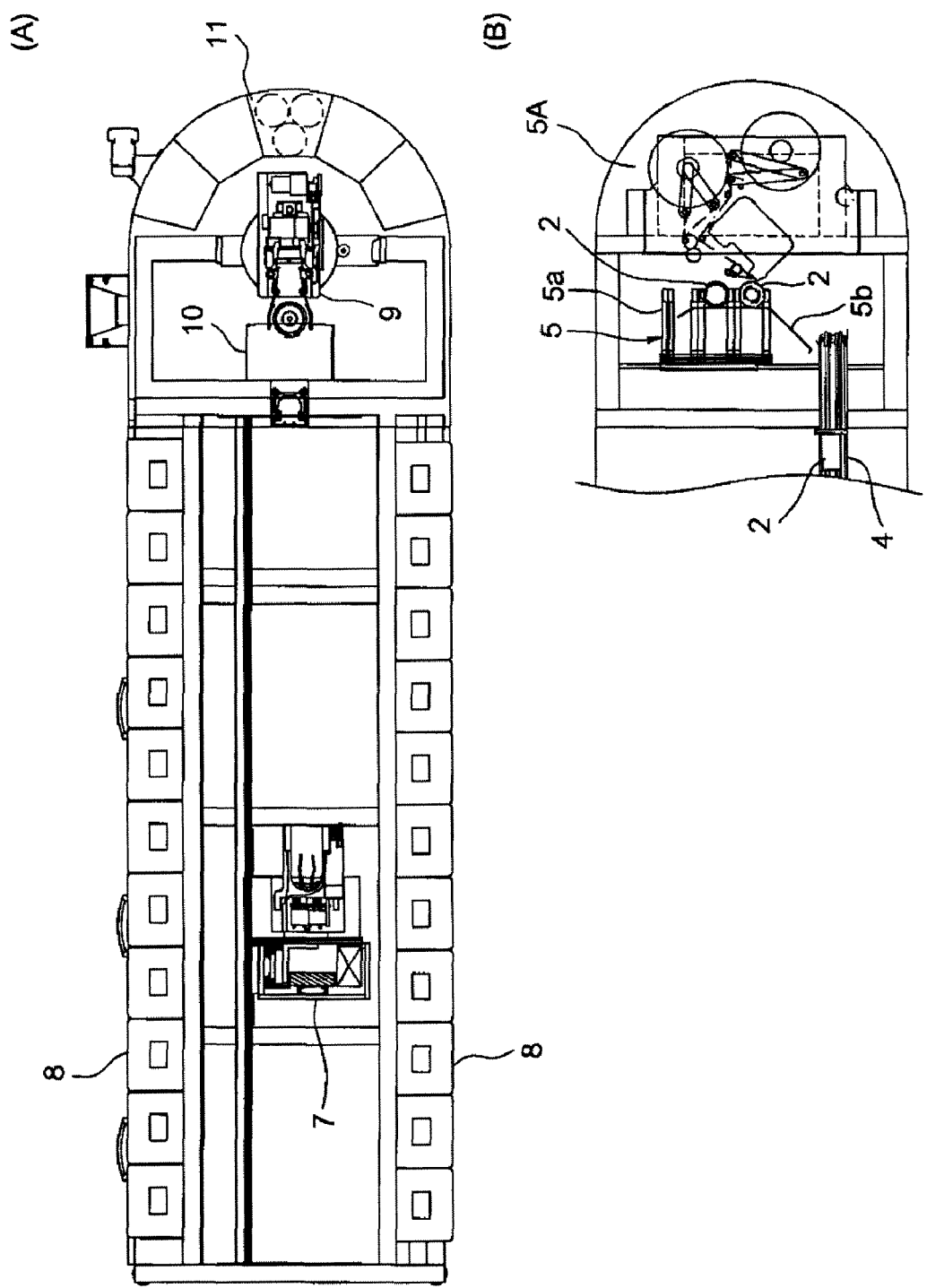
FIG. 3 includes portion (A) showing a sectional view taken along the line IIIA-IIIA of the tablet filling device of FIG. 2, and portion (B) showing a sectional view taken along the line IIIB-IIIB of the tablet filling device of FIG. 2.

As shown in FIGS. 4 through 6, at the vial receiving position P1, the vial 2 is supported by the fork support device 5 of FIG. 3. When, in a state in which the arms 26 are opened within the vial 2 with the vial 2 being held, the feed screw 19 is rotated by the motor 18, the ascent/descent arm 17 and the base plate 24 ascend, enabling the vial 2 to be raised vertically while held by the arms 26. The ascent/descent arm 17 is raised until the frame body 27 abuts against the abutment members 29 before the vial delivery position P2, and the vial 2 is held by a holding device of the third conveyance device 7 of FIG. 2. When, after that, the ascent/descent arm 17 is further raised, but the frame body 27 cannot further ascend while the arms 26 ascend, so the rollers 32 descend with respect to the arms 26 along the guide grooves 26b. The arms 26, which are restricted by the frame body 27, rotate around the rotation shaft 25 against the urging force of the opening spring 31, and are closed so that their forward ends move toward each other. In this way, the friction members 24 of the arms 26 are separated from the inner wall of the vial 2 to release the vial 2, delivering it to the holding device of the third conveyance device 7 of FIG. 2.

Figure 7:
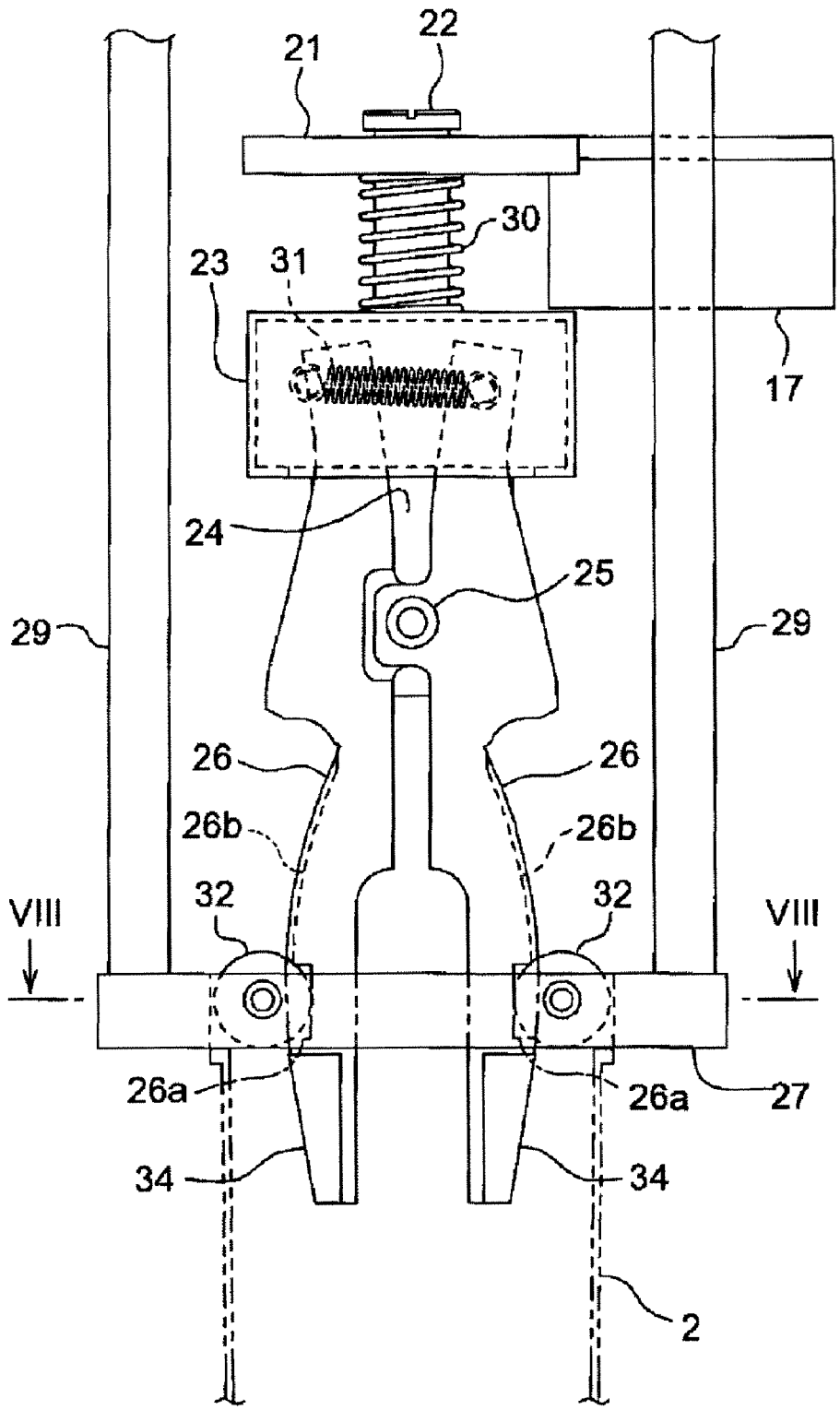
FIG. 7 is an enlarged partial view of the vial conveyance device of FIG. 4 with the arm raised.
Figure 8:
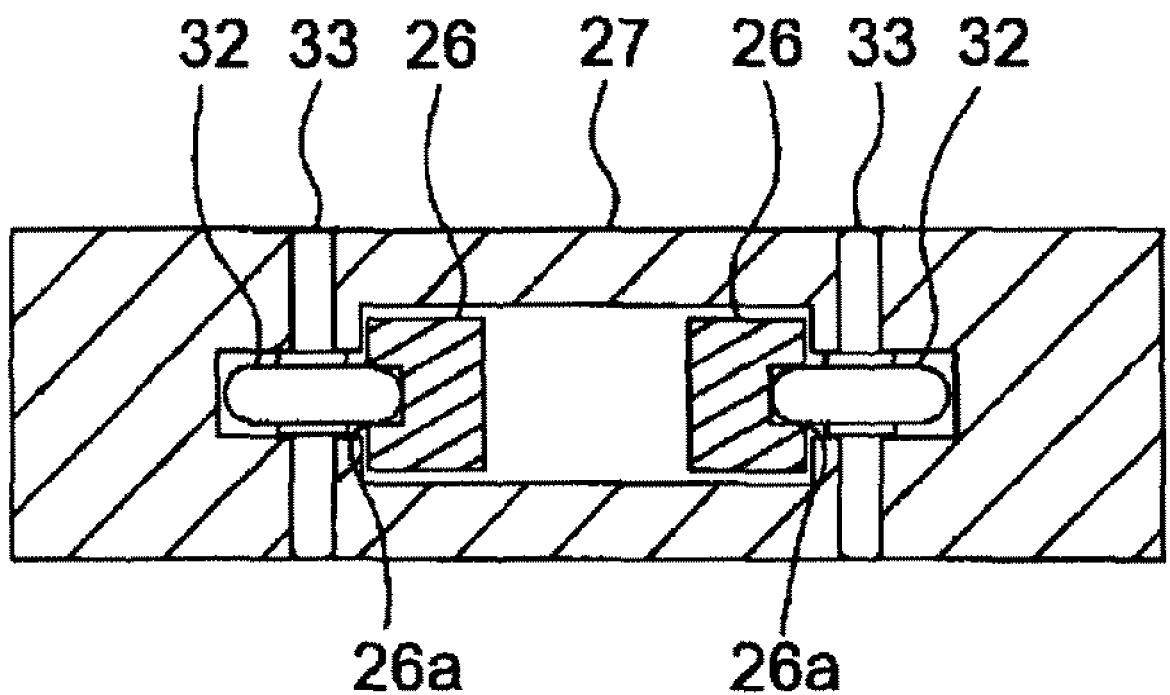
FIG. 8 is a sectional view, taken along the line VIII-VIII, of the vial conveyance device of FIG. 7.

Further, as shown in FIG. 7, the ascent/descent arm 17 ascends to the vial delivery position P2, and the base plate 24 is raised until the rollers 32 of the frame body 27 reach the engagement positions and are engaged with the stopper portions 26a of the arms 26. In this way, once the rollers 32 have been engaged with the stopper portions 26a which are deep grooves, the frame body 27 cannot move relative to the arms 26 unless there is applied a force slightly closing the arms 26 against the urging force of the opening springs 31. Thus, after the holding device of the third conveyance device 7 of FIG. 2 removes the raised vial 2, the motor 18 is rotated in the reverse direction to lower the ascent/descent arm 17, so the arms 26 descend while closed by the frame body 27. When a new vial 2 is supplied to the position to which the arms 26 are to be lowered, the forward end portions of the arms 26 are inserted into the vial 2 immediately before the base plate 24 reaches the vial receiving position P1, and the frame body 27 abuts against the opening edge portion 2a at the top of the vial 2. When the ascent/descent arm 17 is further lowered, the rollers 32 leave the stopper portions 26a of the arms 26 to run onto the guide grooves 26b, thus slightly closing the arms 26. In this way, the rollers 32 are detached from the stopper portions 26a to move into the guide grooves 26b, easily ascending along the guide grooves 26b to enable the frame body 27 to move to the release position. In particular, when the rotation shaft 25 is approached, an abutting direction of the guide grooves 26b with respect to the rollers 32 becomes more upward than an opening direction around the rotation shaft of the abutment portions, forming a pressure angle pushing up the rollers 32. In this way, the rollers 32 are caused to ascend along the guide grooves 26b by the urging force of the opening spring 31. When the base plate 24 descends to the vial receiving position P1, the frame body 17 moves to the release position near the upper ends of the guide grooves 26b as shown in FIG. 7. As a result, the arms 26 are opened such that the friction members 24 are brought into contact with the inner surface of the vial 2, thereby holding the vial 2.

As described above, the vial conveyance device 6 of this embodiment has no drive device such as an actuator on the ascent/descent arm 17, and is lightweight, so the motor 18 may be of small capacitance. Since there is no need to provide wiring for control and power supply on the ascent/descent arm 17, such attachment as a flexible cable duct does not required, resulting in a simple structure. Further, in order to move the frame body 27 to the engagement position or the release position, that is, in order to effect engagement with the stopper portions 26*a* or detachment from the guide grooves 26*b*, the vertical movement of the base plate 24 through the ascent/descent arm 17 by the motor 18 for vertically conveying the vial 2, and a restriction operation member 19 which is a simple stationary structure, and the opening edge portion 2*a* of the vial 2 which is an object of conveyance, are utilized, so there is no need for a special power source or control to hold or release the vial 2. Therefore, the construction of the vial conveyance device 6 as a whole is simplified, and the burden on the control device is small.

While in this embodiment the arms 26 are urged in an opening direction by the opening spring 31, and abut against the inner surface of the vial 2 to hold it through friction, it is also possible for a pair of arms urged in a closing direction to hold the vial 2 therebetween, and for the frame body to be engaged in the inner side of the pair of arms.

Further, while in the above embodiment the abutment members 29 are stationary, and the frame body 27 abut against the abutment members 29 while the arms 26 are moving, it is also possible to move the abutment members 29 to abut against the frame body 27 while the arms 29 remain stationary at the vial receiving position P1 or the vial delivery position P2. This makes it possible to move the frame body 27 in an arbitrary direction without being restricted by the moving direction of the arms 26. Further, it is possible to achieve an increase in degree of freedom in terms of the conveying direction and route for the vial 2 and the design of the configuration of the arms 26 and the frame body 27. Further, while in this embodiment the friction members 34 of the forward ends of the arms 26 and the wall surface of the vial slightly rub each other, the friction members 34 and the vial 2 cease to rub each other by operating the abutment members to move the frame body 27 when the base plate 24 is at rest at the vial receiving position P1 or the vial delivery position P2.

Further, while in this embodiment the opening edge portion 2*a* of the vial 2 is utilized as the first abutment member, it is also possible, as indicated by the chain double-dashed lines in FIG. 6, to adopt stationary abutment member provided in the same height as the opening edge portion 2*a* of the vial 2.

The invention claimed is:

1. A vial conveyance device for conveying a vial from a receiving position to a delivery position, comprising:
    at least two arms that open and close so as to hold and release the vial, at least one of the arms including a frame body stopper;
    an urging member that moves the arms so as to hold the vial;
    a frame body that reciprocates parallel to a conveying direction of the vial to open and close the arms, and is configured to abut against a first abutment member of the vial when the arms move to a receiving position to release the frame body from the frame body stopper and to hold the vial with the arms;
    an arm moving device that moves the arms to the receiving position and a delivery position for the vial; and
    a second abutment member that abuts against the frame body when the arms move to the delivery position to engage the frame body with the frame body stopper and to release the arms from the vial,
    wherein the frame body stopper stops the frame body in a state in which the arms release the vial.

2. A vial conveyance device according to claim 1, wherein a guide groove is provided in at least one of the arms to extend in a moving direction of the frame body, and
    wherein the frame body is equipped with a roller rolling in the guide groove.

3. A vial conveyance device according to claim 2, wherein the frame body stopper is formed in the guide groove, and is a recess to be engaged with the roller.

4. A vial conveyance device according to any one of claims 1 through 3, wherein the arm moving device conveys the arms with a forward end thereof directed downwardly.

5. A vial conveyance device according to claim 1, wherein the first abutment member is an opening edge portion of the vial.

6. An arm assembly for a vial conveyance device for conveying a vial from a receiving position to a delivery position, comprising:
    at least two arms that open and close so as to hold and release the vial, at least one of the arms including a frame body stopper;
    an urging member that moves the arms so as to hold the vial;
    a frame body that reciprocates parallel to a conveying direction of the vial to open and close the arms,
    wherein the frame body is configured to abut against an abutment member and to reciprocate to open and close the arms, and
    the frame body stopper stops the frame body in a state in which the arms release the vial.

7. An arm assembly for a vial conveyance device for conveying a vial from a receiving position to a delivery position, comprising:
    at least two arms that open and close so as to hold and release the vial, at least one of the arms including a frame body stopper;
    an urging member that moves the arms so as to hold the vial;
    a frame body that reciprocates parallel to a conveying direction of the vial to open and close the arms,
    wherein the frame body is configured to abut against an abutment member and to reciprocate, when the arms move to the receiving position and the delivery position, to open and close the arms.

8. An arm assembly for a vial conveyance device according to claim 6 or 7, wherein a guide groove is provided in at least one of the arms to extend in a moving direction of the frame body, and
    wherein the frame body is equipped with a roller rolling in the guide groove.

9. An arm assembly for a vial conveyance device according to claim 8, wherein the frame body stopper is formed in the guide groove, and is a recess to be engaged with the roller.

* * * * *